United States Patent [19]

Fujiwara et al.

[11] Patent Number: 4,661,588
[45] Date of Patent: Apr. 28, 1987

[54] 23-O-SUBSTITUTED CARBAMOYL-23-DEMYCINOSYLDE-SMYCOSIN

[75] Inventors: Tatsuro Fujiwara; Kazuyo Ohta; Eiichi Honda; Takao Hirano; Hideo Sakakibara, all of Shizuoka, Japan

[73] Assignee: Toyo Jozo Kabushiki Kaisha, Shizuoka, Japan

[21] Appl. No.: 790,805

[22] Filed: Oct. 25, 1985

Related U.S. Application Data

[63] Continuation of Ser. No. 459,653, Jun. 20, 1983, abandoned.

[30] Foreign Application Priority Data

Jan. 20, 1982 [JP] Japan .................................. 57-7820
May 10, 1982 [JP] Japan .................................. 57-78896
May 10, 1982 [JP] Japan .................................. 57-78897

[51] Int. Cl.$^4$ .......................................... C07H 17/08
[52] U.S. Cl. ............................................ 536/7.1
[58] Field of Search ................. 549/271, 77; 548/204, 548/236; 536/7.1; 514/30

[56] References Cited

FOREIGN PATENT DOCUMENTS 2116545 9/1983 United Kingdom ................. 536/7.1

OTHER PUBLICATIONS

Tetrahedron Letters, No. 54, pp. 4737–4740, 1970, "The Structure of Tylosin[1,2]" by R. B. Morin et al.
The Journal of Antibiotics, vol. XXXIV, No. 10, pp. 1374–1376, "Syntheis of 4'-Deoxymycaminosyl Tylonolide".
Merck Index, 9th ed., pp. 8007–8016.
Remington's Pharm. Science, 15th ed., pp. 1122–1124.

*Primary Examiner*—Alan Siegel
*Attorney, Agent, or Firm*—Young & Thompson

[57] ABSTRACT

Compounds of the formula

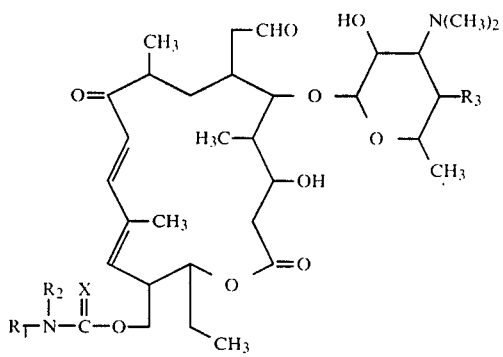

wherein $R_1$ is lower alkyl, lower alkoxycarbonyl-lower alkyl, phenyl, phenyl substituted by one or more lower alkyl or halogen, phenyl-lower alkyl optionally substituted in its side chain by lower alkyl or lower alkoxycarbonyl, thienylmethyl or thiazolyl, $R_2$ is hydrogen or lower alkyl, or

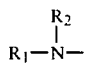

constitutes a 3–7-membered nitrogen-containing heterocyclic ring in which $R_1$ and $R_2$ are connected, $R_3$ is hydrogen or hydroxyl, and X is oxygen or sulfur, or a non-toxic salt thereof. These compounds have stronger antibacterial activity as compared with known clinically used macrolide antibiotics such as erythromycin, oleandomycin, josamycin and leucomycin, and also have strong antibacterial activity against all macrolide antibiotic-resistant strains such as macrolide-resistant A group strains (clinical isolates or erythromycin, oleandomycin and 16-membered macrolide antibiotic resistant strains). These compounds are also stable in vivo and hence may be used for treatment of infectious diseases and also are useful for feed additives and growth stimulants.

2 Claims, No Drawings

23-O-SUBSTITUTED CARBAMOYL-23-DEMYCINOSYLDESMYCOSIN

This application is a continuation of application Ser. No. 459,653, filed Jan. 20, 1983, now abandoned.

This invention relates to novel 23-O-substituted carbamoyl-23-demycinosyldesmycosin derivatives. More particularly, the present invention pertains to compounds of the formula

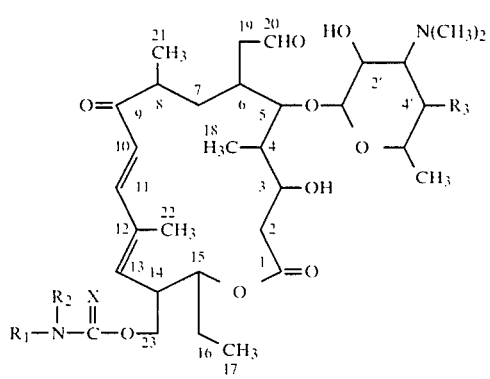

wherein $R_1$ is lower alkyl, lower alkoxycarbonyl-lower alkyl, phenyl, phenyl substituted by one or more lower alkyl or halogen, phenyl-lower alkyl optionally substituted in its side-chain by lower alkyl or lower alkoxycarbonyl, thienylmethyl or thiazolyl, $R_2$ is hydrogen or lower alkyl, or

is 3–7-membered nitrogen-containing heterocyclic ring in which $R_1$ and $R_2$ are connected, $R_3$ is hydrogen or hydroxyl, and X is oxygen or sulfur, or a non-toxic salt thereof.

Examples of pharmaceutically acceptable salts are salts of inorganic acids such as hydrochlorides, sulfates or phosphates and salts of organic acids such as acetates, propionates, tartrates, citrates, succinates, malates, asparatates or glutamates. Other non-toxic salts can be used.

The novel compound [1] has a stronger antibacterial activity as compared with known clinically used macrolide antibiotics such as erythromycin, oleandomycin, josamycin and leucomycin, and also has strong antibacterial activity against all macrolide antibiotic-resistant strains such as macrolide-resistant A group strains (clinical isolates of erythromycin, oleandomycin and 16-membered macrolide antibiotic resistant strains). Furthermore, the above prior-known macrolide antibiotics are affected by chemical modification in vivo or metabolized to change to a compound of weak activity; however the compound [1] is stable in vivo and hence it may be useful for treatment of infectious diseases of human and animals, and also is useful for feed additives and growth stimulants.

A compound [1] of the present invention is produced by any of the following processes: A starting material of the formula

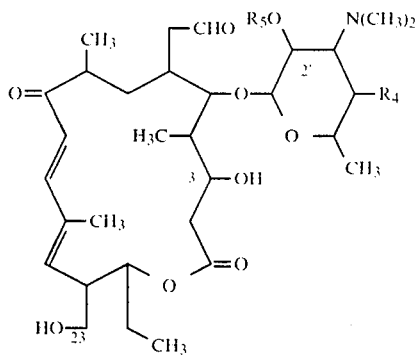

wherein $R_4$ is hydrogen or $-OR_5$ in which $R_5$ is a protective group for hydroxyl, is treated by either of processes (A) or (B) hereinbelow:

(A) A compound [2] hereinabove is tri-lower alkyl-stannylated at the hydroxyl at the 23-position by reacting with bis(tri-lower alkyl tin)oxide in an inert organic solvent under heating, and the compound obtained is reacted with isocyanate of the formula $$R_{11}-N=C=X \qquad [3]$$

wherein $R_{11}$ is lower alkyl, lower alkoxycarbonyl-lower alkyl, phenyl, phenyl substituted by one or more lower alkyl or halogen, phenyl-lower alkyl optionally substituted in its side chain by lower alkyl or lower alkoxy carbonyl, thienylmethyl or thiazolyl, and X has the same meaning as hereinabove; or (B) A compound [2] hereinabove is acetylated, and the obtained acetylated compound is (thio)imidazolidated at the hydroxyl at the 23-position by reacting with 1,1'-(thio)-carbonyl diimidazole in an inert organic solvent, and the thus-obtained compound is reacted with an amine of the formula

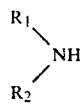

wherein $R_2$ is hydrogen or lower alkyl and $R_1$ has the same meanings as $R_{11}$ hereinabove, or

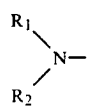

constitutes a 3–7-membered nitrogen-containing heterocyclic ring which $R_1$ and $R_2$ are connected, under heating and the acetal is hydrolyzed. The thus-produced compound [5] of the formula

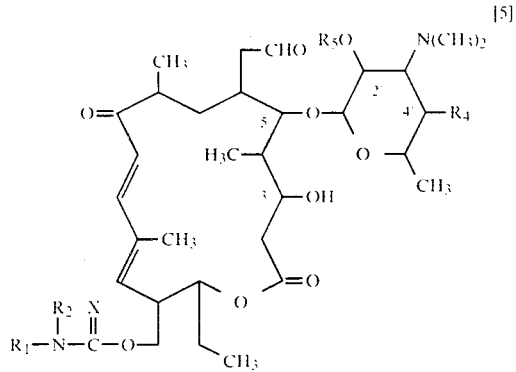

wherein $R_1$, $R_2$, $R_4$, $R_5$ and X have the same meanings as hereinabove, is subjected to dehydrolyzation to remove the hydroxyl group at position-2′ and -4′, or position -2′.

A compound [5] wherein $R_2$ is hydrogen alone can be produced by the above process (A), and the compound [5] wherein $R_2$ is hydrogen or lower alkyl can be obtained by process (B).

The starting material [2] of the present invention wherein $R_4$ is $OR_5$, in which $R_5$ is a protective group for hydroxyl, is a compound in which the hydroxyl at position-2′ and -4′ of 23-demycinosyldesmycosin [Tetrahedron Letters, 4737 (1970)] is protected, and a compound [2] wherein $R_4$ is hydrogen, is a compound in which the hydroxyl at position-2′ of 23-demycinsoyl-4′-deoxydesmycosin [J. Antibiot., 34 (10), 1374–1376 (1981), Jap. Pat. Unexam. Publ. No. 57-28100] is protected.

Examples of protective groups are lower alkanoyls such as acetyl, propionyl or butylyl and halogenated acetyls such as chloroacetyl, dichloroacetyl, trichloroacetyl or trifluoroacetyl. Acetyl is preferred.

The introduction of acetyl can be effected by reacting 23-demycinosyldesmycosin or 23-demycinosyl-4′-deoxydesmycosin with acetic anhydride in an inert organic solvent. Preferred examples of inert organic solvents are dichloromethane, chloroform, dichloroethane or acetone. The reaction proceeds at room temperature, and can be checked by silica gel thin layer chromatography (TLC) or high performance liquid chromatography (HPLC), and can be stopped upon observing the disappearance of 23-demycinosyldesmycosin or 23-demycinosyl-4′-deoxydesmycosin.

Reaction product [2] can be isolated from a reaction mixture by adding water to the reaction mixture and extracting with a water-immiscible organic solvent such as chloroform, dichloroethane, methyl isobutyl ketone, ethyl acetate or butyl acetate at an alkaline pH 8–9.5. Further purification can be effected by column chromatography using silica gel, active alumina or adsorbent resin with an appropriate solvent such as benzeneacetone or chloroform-methanol.

An O-substituted carbamoylation of the hydroxyl group at position-23 of the starting substance [2] is effected by tri-lower alkylstannylation of the said hydroxyl group by reacting with bis(tri-lower alkyl tin)oxide in an inert organic solvent under heating. Examples of inert organic solvent are preferably benzene, toluene or xylene. An example of bis(tri-lower alkyl tin)oxide is bis(tributyl tin)oxide. The heating temperature is preferably the boiling temperature of the solvent or below, and is 80°–110° C. Due to the formation of water during the reaction, an insoluble dehydrating agent such as a molecular sieve is added to the reaction mixture.

The compound [5] wherein $R_2$ is hydrogen can be obtained by O-substituted carbamoylation of the said tri-lower alkyl stannylated compound. The carbamoylation reaction can be conducted without isolating the tri-lower alkyl stannylated compound after isolation of the dehydrating agent, by directly adding an isocyanate of the formula [3] to the reaction mixture.

Examples of isocyanates are methylisocyanate, ethylisocyanate, propylisocyanate, butylisocyanate or ethoxycarbonylmethylisocyanate, phenylisocyanates such as phenylisocyanate, o-, m-, p-tolylisocyanate, 2,3-, 2,4-, 2,5-, 2,6-, 3,4-, 3,5-xylylisocyanate, o-, m-, p-methoxyphenylisocyante, o-, m-, p-chlorophenylisocyanate, o-, m-, p-fluorophenylisocyanate, or 2,3-, 2,4-, 2,5-, 2,6-, 3,4- 3,5-dichlorophenylisocyante, phenyllower alkylisocyanates such as benzylisocyanate, benzylthioisocyanate, α-methyl-benzoylisocyanate, α-methyl-benzylthioisocyanate or β-phenyl-ethylisocyanate, or heterocyclic rings containing isocyanate such as 2-thienylmethylisocyanate or 2-thiazolylisocyanate.

The reaction of the tri-lower alkylstannylated compound and isocyanate [3] proceeds at room temperature. The reaction can be traced by TLC or HPLC and is terminated upon the disappearance of the tri-lower alkylstannylated compound.

Isolation of the reaction product [5] is effected by adding water to the reaction mixture and extracting with a water-immiscible organic solvent such as chloroform, methyl isobutyl ketone, ethyl acetate or butyl acetate. Further purification can be effected by column chromatography using silica gel, active alumina or an absorption resin and eluting with benzene-acetone.

The compound [5] can be produced by another process, namely: protecting the aldehyde group of compound [2] by acetylation, (thio) imidazolidating the hydroxyl group at position -23 by reacting with 1,1′-(thio)carbonyldiimidazole in an inert organic solvent, reacting the thus-obtained (thio) imidazolidated compound with amine [4] under heating, and hydrolyzing the acetal.

The above acetylation can be performed by known processes of changing aldehyde to acetal, for example condensation of the compound [2] and a lower alcohol using a catalyst such as ferric chloride, ammonium chloride, hydrogen chloride, trifluoroacetic acid or sulfuric acid, or condensation with an orthoformic acid ester using a catalyst such as mineral acid.

Thio-imidazolidation of the hydroxyl at position-23 can be effected by reacting the above acetal with 1,1′-(thio)-carbonyldiimidazole in an inert organic solvent. Examples of inert organic solvents are halogenated hydrocarbons such as dichloromethane, chloroform or dichloroethane. The reaction proceeds at room temperature and can be traced by TLC or HPLC and is stopped upon the disappearance of acetal.

The thus-obtained (thio)immidazolidated compound can be used either without isolation from the reaction mixture or after isolation for the next step of reaction with amine [4]. Isolation of the (thio)imidazolidated compound can be effected by pouring water into the reaction mixture, adjusting the aqueous phase to pH 8.0–9.5, extracting with an organic solvent and distilling off the solvent. Higher boiling organic solvents such as dichloroethane can preferably be used in the reaction of acetal and 1,1′-(thio)carbonyldiimidazole in the case of direct reaction with the amine without isolating the (thio)imidazolidated compound.

Examples of the amine [4] are lower alkylamines such as methyamine, ethylamine, propylamine, butylamine or ethoxycarbonyl methylamine, phenylamines such as aniline, o-, m-, p-toluidine, 2,3-, 2,4-, 2,5-, 2,6-, 3,4-, 3,5-xylidine, o-, m-, p-anisidine, o-, m-, p-chloroaniline, o-, m-, p-fluoroaniline, 2,3-, 2,4-, 2,5-, 2,6-, 3,4-, 3,5-dichloroaniline or N-methylaniline, phenyl lower alkylamines such as benzylamine, β-phenylethylamine, α-methylbenzylamine, N-methylbenzylamine or α-methoxycarbonyl benzylamine, heterocyclic ring-containing amines such as 2-thienylmethylamine or 2-aminothiazole, and alkyleneimines such as azetidine, pyrrolidine, piperidine, hexamethyleneimine or heptamethyleneimine.

The reaction of the above (thio)imidazolidated compound and amine [4] proceeds in an inert organic solvent under heating. Examples of inert organic solvents are dichloroethane, benzene, toluene or dioxane. The heating temperature is the boiling point of the organic solvent or below, usually 70°–90° C.

Compound [5] can be obtained by hydrolyzing the acetal group of the thus-obtained 23-O-substituted (thio)carbamoylated compound.

Hydrolysis can be effected by known methods such as the acid hydrolysis of acetal to acealdehyde. The reaction can be traced by silica-gel TLC and is terminated upon the disappearance of acetal. Isolation of the product [5] can be effected in the same way as hereinbefore explained.

Removal of the protective group of the hydroxyl at position-2′ and -4′, or position-2′, such as acetyl, of compound [5] can be effected by heating in lower alcohol, for example methanol or ethanol, preferably methanol. The removal reaction can be traced by TLC or HPLC and is terminated upon the disappearance of compound [5].

Isolation of compound [1] can be performed by known methods of macrolide antibiotic isolation, for example concentration, extraction washing, transfer extraction and recrystallization, or chromatography using silica gel, active alumina or an adsorption resin.

The minimum inhibitory concentration (MIC, μg/ml) of compound [1] of the present invention is exemplified in the following table. The numbers in the table have the following meanings:

| | $R_1-\underset{\underset{R_2}{|}}{N}-\underset{\underset{}{\overset{X}{\|}}}{C}-$ | $R_3$ |
|---|---|---|
| 1. | $CH_3(CH_2)_2NHCO-$ | OH |
| 2. | $CH_3(CH_2)_3NHCO-$ | OH |
| 3. | $\underset{CH_2NHCO-}{\overset{COOC_2H_5}{\|}}$ | OH |
| 4. | 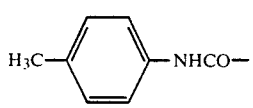 | OH |
| 5. | 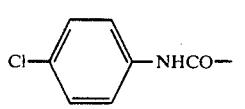 | OH |
| 6. | 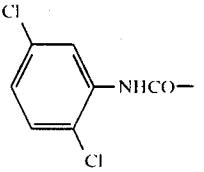 | OH |
| 7. | 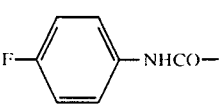 | OH |
| 8. | 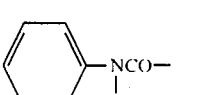 | OH |
| 9. | 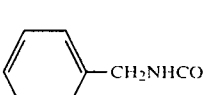 | OH |
| 10. | 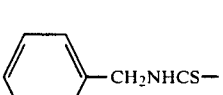 | OH |
| 11. | 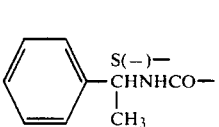 | OH |
| 12. | 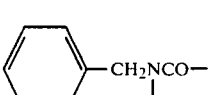 | OH |
| 13. | 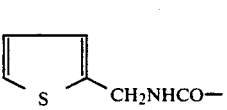 | OH |
| 14. | 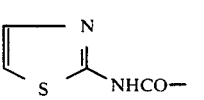 | OH |
| 15. | 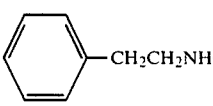 | OH |
| 16. | 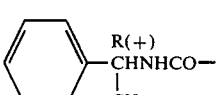 | OH |
| 17. | 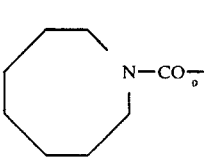 | OH |

-continued

| | $R_2$ $X$ $\|$ $\|$ $R_1-N-C-$ | |
|---|---|---|
| | | $R_3$ |
| 18. | 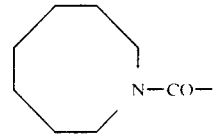N—CO— | OH |
| 19. | 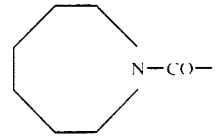N—CO— | H |
| 20. | 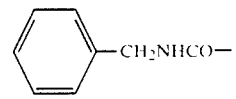—CH$_2$NHCO— | H |
| 21. | Cl—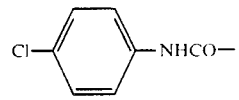—NHCO— | H |
| 22. | 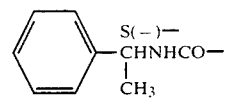—CHNHCO—$\underset{CH_3}{\overset{S(-)-}{\|}}$ | H |

*macrolide A group resistant strain (clinical isolates of erythromycin, oleandomycin and 16-membered macrolide antibiotic resistant strain).

The following examples illustrate the present invention. The Rf values are measured by the following TLC conditions, if not specified:
Carrier: Merck, DC-Fertigplatten Kiesel gel 60 F$_{254}$ Art 5715.
Developer:
  a: chloroform-methanol-conc. aq. ammonia (100:10:1)
  b: chloroform-methanol-conc. aq. ammonia (150:10:1)
  c: hexane-benzene-acetone-ethyl acetate-methanol (90:80:25:60:30)
  d: benzene-acetone (3:1)
  e: benzene-acetone (2:1)
  f: chloroform-methanol (10:1)
  g: chloroform-methanol (20:1)

EXAMPLE 1

2′,4′-O-diacetyl-23-demycinosyldesmycosin

Acetic anhydride (16.73 ml, 5 molar excess) was added to 23-demycinosyldesmycosin (21.21 g, 35.5 mM) dissolved in dichloromethane (106 ml) and the mixture was stirred at room temperature for 1.5 hour. The reaction mixture was poured into dilute aqueous ammonia (400 ml) and extracted with chloroform (300 ml). The aqueous layer was again extracted with chloroform (300 ml) and combined with the previous extract. The mixed extract was dired with anhydrous megnesium phosphate and dried in vacuo to obtain 2′,4′-O-diacetyl-23-demycinosyldesmycosin (24.0 g, yield: 99.3%).
TLC: Rf$_b$=0.13, Rf$_d$=0.32.

| Test organisms | compound | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Staph. aureus ATCC6538P | 0.2 | 0.1 | 0.8 | 0.1 | 0.1 | 0.1 | 0.1 | ≦0.05 | ≦0.05 | 0.2 | 0.1 | ≦0.05 |
| Staph. aureus MS353 | 0.2 | 0.2 | 0.8 | 0.2 | 0.1 | 0.1 | 0.1 | ≦0.05 | 0.1 | 0.2 | 0.1 | ≦0.05 |
| Staph. aureus MS353AO* | >100 | >100 | 12.5 | 100 | .50 | 25 | >100 | 100 | >100 | 12.5 | 25 | >100 |
| Staph. aureus O127* | >100 | >100 | 50 | 100 | .50 | 25 | >100 | >100 | >100 | 25 | 50 | >100 |
| Staph. epidermidis ap-al-/ | ≦0.05 | ≦0.05 | 0.4 | ≦0.05 | ≦0.05 | ≦0.05 | ≦0.05 | ≦0.05 | ≦0.05 | 0.1 | ≦0.05 | ≦0.05 |
| Strept. pyogenes N.Y.5 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| Strept. pyogenes 1022* | 100 | 50 | 0.4 | 50 | 1.6 | 3.1 | 50 | >100 | >100 | 3.1 | 50 | >100 |
| Strept. faecalis 1501 | 0.4 | 0.4 | 0.8 | 0.4 | 0.8 | 0.2 | 0.2 | ≦0.05 | ≦0.05 | 0.2 | ≦0.05 | 0.1 |
| Strept. agalactiae 1020 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| Sarcina lutea ATCC9341 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| Coryn. diphtheriae P.W.8 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| Bacillus subtilis ATCC6633 | 0.2 | 0.2 | 0.8 | 0.2 | 0.1 | 0.1 | 0.2 | ≦0.05 | 0.1 | 0.2 | 0.1 | 0.1 |
| E. coli NIHJ-JC2 | 50 | 50 | >100 | 50 | 25 | 50 | 50 | 100 | 25 | 50 | 50 | 50 |
| Salm typhosa H901 | 100 | 100 | >100 | 100 | 50 | >100 | 100 | 100 | 50 | >100 | 100 | 100 |
| Kleb. pneumoniae ATCC10031 | 6.3 | 3.1 | 12.5 | 3.1 | 3.1 | 3.1 | 3.1 | 25 | 3.1 | 6.3 | 6.3 | 25 |
| Shigella sonnei E33 | 50 | 50 | >100 | 50 | 25 | 50 | 25 | 50 | 25 | 50 | 50 | 50 |
| Proteus vulgaris OX19 | 12.5 | 12.5 | 25 | 12.5 | 3.1 | 12.5 | 12.5 | 12.5 | 6.3 | 12.5 | 12.5 | 6.3 |
| Ps. aeruginosa IAM1095 | 100 | 100 | 100 | 100 | 50 | >100 | 100 | 100 | 12.5 | >100 | 50 | 100 |

| Test organisms | compound | | | | | | | | | | Erythromycin | Tylosin |
|---|---|---|---|---|---|---|---|---|---|---|---|---|
| | 13 | 14 | 15 | 16 | 17 | 18 | 19 | 20 | 21 | 22 | | |
| Staph. aureus ATCC6538P | 0.1 | 0.1 | ≦0.05 | 0.1 | ≦0.05 | ≦0.05 | ≦0.05 | ≦0.05 | ≦0.05 | 0.1 | 0.1 | 0.8 |
| Staph. aureus MS353 | 0.1 | 0.2 | ≦0.05 | 0.1 | ≦0.05 | ≦0.05 | ≦0.05 | ≦0.05 | ≦0.05 | 0.1 | 0.1 | 0.8 |
| Staph. aureus MS353AO* | >100 | >100 | 0.1 | >100 | >100 | >100 | >100 | 3.1 | >100 | 50 | >100 | >100 |
| Staph. aureus O127* | >100 | 50 | >100 | >100 | >100 | >100 | >100 | >100 | >100 | 50 | >100 | >100 |
| Staph. epidermidis ap-al-/ | ≦0.05 | ≦0.05 | ≦0.05 | ≦0.05 | ≦0.05 | ≦0.05 | ≦0.05 | ≦0.05 | ≦0.05 | ≦0.05 | 0.1 | 0.4 |
| Strept. pyogenes N.Y.5 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | 0.1 |
| Strept. pyogenes 1022* | >100 | >100 | 100 | >100 | 3.1 | 3.1 | 100 | 3.1 | 0.2 | 25 | 50 | 25 |
| Strept. faecalis 1501 | 0.1 | 0.1 | 0.1 | ≦0.05 | 0.1 | 0.1 | 0.1 | ≦0.05 | 0.1 | 0.4 | 0.2 | 1.6 |
| Strept. agalactiae 1020 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | 0.4 |
| Sarcina lutea ATCC9341 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| Coryn. diphtheriae P.W.8 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| Bacillus subtilis ATCC6633 | 0.1 | 0.2 | 0.1 | 0.1 | 0.1 | 0.1 | ≦0.05 | ≦0.05 | 0.1 | 0.1 | ≦0.05 | 0.2 |
| E. coli NIHJ-JC2 | 50 | 100 | 50 | 100 | 100 | 50 | 12.5 | 25 | 50 | 25 | 50 | >100 |
| Salm. typhosa H901 | 100 | 100 | 100 | 100 | 100 | >100 | 25 | 50 | 100 | 25 | 50 | >100 |

| | | | | | | | | | | | |
|---|---|---|---|---|---|---|---|---|---|---|---|
| -continued | | | | | | | | | | | |
| Kleb. pneumoniae ATCC10031 | 6.3 | 3.1 | 1.0 | 12.5 | 3.1 | 3.1 | 1.6 | 1.6 | 3.1 | 3.1 | 6.3 | 100 |
| Shigella sonnei E33 | 50 | 50 | 50 | 50 | 50 | 50 | 12.5 | 12.5 | 25 | 12.5 | 50 | >100 |
| Proteus vulgaris OX19 | 6.3 | 12.5 | 6.3 | 12.5 | 50 | 50 | 3.1 | 3.1 | 6.3 | 3.1 | 25 | >100 |
| Ps. aeruginosa IAM1095 | 50 | 100 | 50 | 100 | 50 | 50 | 25 | 50 | 100 | 50 | 100 | >100 |

EXAMPLE 2

23-O-(2,5-dichlorophenylcarbamoyl)-23-demycinosyldesmycosin

Bis(tributyl tin)oxide (37.35 μl) and small amount of 3 Å molecular sieve were added to 2',4'-O-diacetyl-23-demycinosyldesmycosin (1 g, 1.466 mM) dissolved in toluene (20 ml), and the mixture was refluxed at 120°–130° C. for 2 hours. The molecular sieve was removed and 2,5-dichlorophenylisocyanate (413.4 mg, 1.5 molar excess) was added to the filtrate and the mixture was stirred at room temperature for 2 hours. The reaction mixture was poured into dilute aqueous ammonia (100 ml) and extracted twice with chloroform (50 ml). The chloroform layer was dried with anhydrous magnesium sulfate and concentrated in vacuo. The residue, dissolved in a small amount of benzene, was charged on a column of silica gel (50 g) and eluted with benzene-acetone (10:1). The fractions showing Rf 0.39 were collected and dried in vacuo. The thus-obtained 2',4'-O-diacetyl-23-O-(2,5-dichlorophneyl carbamoyl)-23-demycinosyldesmycosin dissolved in methanol (20 ml) was refluxed at 65° C. overnight. The reaction mixture was added to dilute aqueous ammonia (60 ml) and extracted twice with chloroform (50 ml). The chloroform layer was dehydrated by adding anhydrous magnesium sulfate and concentrated in vacuo. The residue, dissolved in a small amount of chloroform, was charged on a column of silica gel (50 g) and chromatographed by chloroform-methanol (40:1 to 20:1). The fractions showing $Rf_b$ 0.42 were collected and concentrated in vacuo to obtain 23-O-(2,5-dichlorophenylcarbamoyl)-23-demycinosyldesmycosin (264.2 mg, yield: 22.9%).

TLC: $Rf_b=0.42$, $Rf_c=0.07$.

NMR (100 MHz, $CDCl_3$) $\delta_{ppm}$; 1.83 (s., 3H), 2.51 (s., 6H), 4.26 (d., 2H), 4.27 (d., 1H), 4.97 (m., 1H), 5.83 (d., 1H), 6.30 (d., 1H), 6.99 (d. d.,=1H), 7.16 (s., 1H), 7.28 (d., 1H), 7.32 (d., 1H), 8.20 (d., 1H), 9.70 (s., 1H).

EXAMPLE 3

2',4'-O-diacetyl-23-O-butylcarbamoyl-23-demycinosyldesmycosin

Bis(tributyl tin)oxide (994.6 μl) and a small amount of 3 Å molecular sieve were added to 2',4'-O-diacetyl-23-demycinosyldesmycosin (2.663 g, 3.904 mM) dissolved in toluene (56 ml) and the mixture was refluxed in an oil bath for 2 hours. After filtering off the molecular sieve, butylisocyanate (89.6 μl, 1.5 molar excess) was added to ⅛ the amount of the filtrate and the mixture was stirred at room temperature for 2 hours. The reaction mixture was added to dil. aqueous ammonia (20 ml) and extracted twice with chloroform (20 ml). After drying the chloroform layer with anhydrous magnesium sulfate, it was concentrated in vacuo. The residue was charged on a silica gel plate (Merck, Art 5717) and developed with benzene-acetone (3:1). The band showing Rf 0.55 was scratched to collect the same and extracted with chloroform-methanol (2:1). The eluate was dried in vacuo to obtain 2',4'-O-diacetyl-23-O-butylcarbamoyl-23-demycinosyldesmycosin (286.3 mg, yield: 75.1%).

TLC: $Rf_d=0.55$.

In the above Example 3, butylisocyanate was replaced by p-chlorophenylisocyanate (112.4 mg), p-fluorophenylisocyanate (83.3 μl), p-tolylisocyanate (92.4 μl), S-(−)-α-methylbenzylisocyanate (107.7 μl), ethoxycarbonyl methylisocyanate (94.6 μl), propylisocyanate (62.3 μl) and benzylthioisocyanate (109.8 μl), respectively, to obtain the compounds of the following Examples 4–10, respectively:

EXAMPLE 4

2',4'-O-diacetyl-23-O-(p-chlorophenyl carbamoyl)-23-demycinosyldesmycosin (266.9 mg, yield: 65.4%), TLC: $Rf_d=0.61$.

EXAMPLE 5

2',4'-O-diacetyl-23-O-(p-fluorophenyl carbamoyl)-23-demycinosyldesmycosin (231.1 mg, yield: 57.8%), TLC: $Rf_d=0.59$.

EXAMPLE 6

2',4'-O-diacetyl-23-O-(p-tolyl carbamoyl)-23-demycinosyldesmycosin (208.3 mg, yield: 52.3%), TLC: $Rf_d=0.61$.

EXAMPLE 7

2',4'-O-diacetyl-23-O-[S(−)-α-methylbenzyl carbamoyl]-23-demycinosyldesmycosin (174.3 mg, yield: 43.1%), TLC: $Rf_d=0.56$.

EXAMPLE 8

2',4'-O-diacetyl-23-O-ethoxycarbonylmethyl carbamoyl-23-demycinosyldesmycosin (172.2 mg, yield: 43.5%), TLC: $Rf_d=0.46$.

EXAMPLE 9

2',4'-O-diacetyl-23-O-propylcarbamoyl-23-demycinosyldesmycosin (220.4 mg, yield: 58.9%), TLC: $Rf_d=0.52$.

EXAMPLE 10

2',4'-O-diacetyl-23-O-benzylthio carbamoyl-23-demycinosyldesmycosin (131.1 mg, yield: 32.3%), TLC: $Rf_d=0.67$.

EXAMPLE 11

23-O-butylcarbamoyl-23-demycinosyldesmycosin

Methanol (5 ml) was added to 2',4'-diacetyl-23-O-butylcarbamoyl-23-demycinosyldesmycosin (266.3 mg), and the mixture was stirred at 55° C. overnight. The reaction mixture was concentrated in vacuo and the residue, dissolved in chloroform (20 ml), was washed with dil. aq. ammonia. The aqueous layer was again extracted with chloroform (20 ml) and combined with the previous extract, dried with anhydrous magnesium sulfate then dried in vacuo to obtain 23-O-butyl carbamoyl-23-demycinosyldesmycosin (206.0 mg, yield: 86.7%).

TLC: $Rf_b=0.35$.

NMR (100 MHz, $CDCl_3$) $\delta_{ppm}$; 1.8.0 (s., 3H), $CH_3$-12), 2.50 (s., 6H,-N $(CH_3)_2$), 4.17 (br. m., 2H,H-23), 4.25

(d., 1H, J=7.3 Hz, H-1), 4.75 (br. m., 1H, NH), 4.84 (m., 1H, H-15), 5.83 (d., 1H, J=11.0 Hz, H-13), 6.28 (d., 1H, J=15.7 Hz, H-10), 7.30 (d., 1H, J=15.7 Hz, H-11), 9.70 (s., 1H, CHO).

In the above Example 11, 2′,4′-O-diacetyl-23-O-butyl-carbamoyl-23-demycinosyldesmycosin was replaced by the compound of Example 4 (246.9 mg), the compound of Example 5 (197.8 mg), the compound of Example 6 (175.0 mg), the compound of Example 7 (141.0 mg), the compound of Example 8 (138.2 mg), the compound of Example 9 (187.1 mg) and the compound of Example 10 (117.7 mg), respectively, ot obtain the product in the following Examples 12–18.

EXAMPLE 12

23-O-(p-chlorophenyl carbamoyl)-23-demycinosyldesmycosin: 171.8 mg, yield: 77.4%.

TLC: $Rf_b = 0.32$.

NMR (100 MHz, CDCl$_3$) $\delta_{ppm}$; 1.82 (s., 3H, CH$_3$-12), 2.50 (s., 6H, N(CH$_3$)$_2$), 4.25 (br. m., 2H, H-23), 4.25 (d., 1H, J=7.3 Hz, H-1′), 4.98 (m., 1H, H-15), 5.87 (d., 1H, J=10.8 Hz, H-13), 6.30 (d., 1H, J=15.7 Hz, H-10), 7.10 (s., 1H, NH), 7.23 (d., 2H, p-chlorophenyl 3,5-H), 7.30 (d., J=15.7 Hz, H,-11), 7.30 (d., 2H, p-chlorophenyl 2,6-H), 9.69 (s., 1H, CHO).

EXAMPLE 13

23-O-(p-fluorophenylcarbamoyl)-23-demycinosyldesmycosin: 158.2 mg, yield: 89.1%.

TLC: $Rf_b = 0.31$.

NMR (100 MHz, CDCl$_3$) $\delta_{ppm}$; 1.82. (s., 3H, CH$_3$-12), 2.50 (s., 6H, N (CH$_3$)$_2$), 4.25 (br. m., 2H, H-23), 4.25 (d., 1H, J=7.1 Hz, H-1′), 4.98 (m., 1H, H-15), 5.87 (d., 1H, J=10.1 Hz, H-13), 6.30 (d., 1H, J=16.0 Hz, H-10), 6.9~7.1 (m., 3H, NH and p-fluorophenyl 3,5-H), 7.2~7.4 (m., 2H, p-fluorophenyl 2,6-H), 7.31 (d., 1H, J=16.0 Hz, H-11), 9.70 (s., 1H, CHO).

EXAMPLE 14

23-O-(p-tolylcarbamoyl)-23-demycinosyldesmycosin: 142.2 mg, yield: 90.6%.

TLC: $R_b = 0.35$.

NMR (100 MHz, CDCl$_3$) $\delta_{ppm}$; 1.82. (s., 3H, CH$_3$-12), 2.30 (s., 3H,

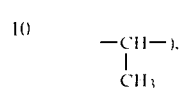

2.50 (s., 6H, N(CH$_3$)$_2$), 4.25 (m., 2H, H-23), 4.25 (d., 1H, J=7.1 Hz, H-1′), 4.98 (m., 1H, H-15), 5.86 (d., 1H, J=10.8 Hz, H-13), 6.29 (d., 1H, J=15.7 Hz, H-10), 6.76 (br.s., 1H, NH), 7.10 (d., 1H, p-tolyl 3,5-H), 7.27 (d., 2H, p-tolyl 2,6-H), 7.31 (d., 1H, J=15.7 Hz, H-11), 9.69 (s., 1H, CHO).

EXAMPLE 15

23-O-[S(−)-α-methylbenzyl carbamoyl]-23-demycinosyldesmycosin: 11.3 6 mg, yield: 89.6%.

TLC: $Rf_b = 0.36$.

NMR (100 MHz, CDCl$_3$) $\delta_{ppm}$; 1.48 (d., 3H, J=6.9 Hz,

1.74 (s., 3H, CH$_3$-12), 2.49 (s., 6H, N(CH$_3$)$_2$), 4.11 (m., 2H, H-23), 4.25 (d., 1H, J=7.4 Hz, H-1′), 4.6~5.2 (m., 5H, H-15, NH,

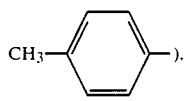

5.79 (d., 1H, J=10.6 Hz, H-13), 6.27 (d., 1H, J=15.5 Hz, H-10), 7.28 (d., 1H, J=15.5 Hz, H-11), 7.30 (s., 5H, phenyl proton), 9.70 (s., 1H, CHO).

EXAMPLE 16

23-O-ethoxycarbonylmethyl carbamoyl-23-demycinosyldesmycosin: 111.6 mg, yield: 89.6%.

TLC: $Rf_b = 0.30$.

NMR (100 MHz, CDCl$_3$) $\delta_{ppm}$; 1.29 (t., 3H, J=7.1 Hz, CH$_3$CH$_2$—), 1.81 (s., 3H, CH$_3$-12), 2.50 (s., 6H, N(CH$_3$)$_2$), 3.94 (d., 2H, J=5.9 Hz., —CH$_2$NH—), 4.20 (m., 2H, H-23), 4.22 (q., J=7.1 Hz, CH$_3$CH$_2$—), 4.27 (d., 1H, J=7.3 Hz, H-1′), 4.96 (m., 1H, H-15), 5.29 (br. t., 1H, NH), 5.81 (d., 1H, J=9.8 Hz, H-13), 6.29 (d., 1H, J=15.5 Hz, H-0), 7.30 (d., 1H, J=15.5 Hz, H-11), 9.70 (s., 1H, CHO).

EXAMPLE 17

23-O-propylcarbamoyl-23-demycinosyldesmycosin: 145.2 mg, yield: 87.1%.

TLC: $Rf_b − 0.32$.

NMR (100 MHz, CDCl$_3$) $\delta_{ppm}$; 1.80 (s., 3H, CH$_3$-12), 2.50 (s., 6H, N(CH$_3$)$_2$), 4.16 (br.m., 2H, H-23), 4.25 (d., 1H, J=7.6 Hz, H-1′), 4.80 (br.m., 1H, NH), 4.95 (m., 1H, H-15), 5.83 (d., 1H, J=10.3 Hz, H-13), 6.29 (d., 1H, J=15.5 Hz, H-10), 7.30 (d., 1H, J=15.5 Hz, H-11), 9.69 (s., 1H, CHO).

EXAMPLE 18

23-O-benzylthiocarbamoyl-23-demycinosyldesmycosin: 97.0 mg, yield: 91.6%.

TLC: $Rf_b = 0.37$.

EXAMPLE 19

2′,4′-O-diacetyl-23-O-(1-imidazolecarbonyl)-23-demycinosyldesmycosin dimethylacetal 2′,4′-O-diacetyl-23-demycinosyldesmycosin (5 g) was dissolved in a mixture of trifluoroacetic acid (2.5 ml) and methanol (100 ml), and the mixture was stirred at room temperature for 4.5 hours. The reaction mixture was checked by TLC developing with chloroform-methanol (20:1) for complete conversion to dimethylacetal, and poured into alkaline ice water (pH 9–10 by aq. ammonia, 250 ml), and extracted twice with chloroform (250 ml). The chloroform layer was dehydrated with anhydrous magnesium sulfate and dried in vacuo to obtain foamy 2′,4′-O-diacetyl-23-demycinosyldesmycosin dimethylacetal, which was dissolved immediately in dichloroethane (25 ml). The solution was added dropwise to a dichloroethane (50 ml) solution of 1,1′-carbodiimidazole (1189 mg, equimolar amount). Then the mixture was stirred at 50° C. for 1 hour. The reaction mixture was checked by silica gel TLC developed with chloroform-methanol (20:1) for the end point of the reaction, and washed with dil. HCl (pH 2-3) and dil. aq. ammonia (pH 8-10). After dehydration with anhydrous magnesium sulfate, the solution was dried in vacuo to obtain powdered 2′,4′-O-diacetyl-23-O-(1-imidazolecarbonyl)-23-demycinosyldesmycosin dimethylacetal (4.43 g).

TLC: $Rf_g = 0.50$.

NMR (100 MHz, CDCl$_3$) $\delta_{ppm}$; 1.83 (s., 3H), 2.05 (s., 6H), 2.34 (s., 6H), 3.21 (s., 3H), 3.29 (s., 3H), 4.38 (d., 1H), 4.49 (2H), 5.76 (d., 1H), 6.32 (d., 1H), 7.09 (s., 1H), 7.24 (d., 1H), 7.37 (s., 1H), 8.10 (s., 1H).

EXAMPLE 20

23-O-benzylcarbamoyl-23-demycinosyldesmycosin

The acetalated compound (200 mg) in Example 19 and benzylamine (0.04 ml) were added to dichloroethane (2.6 ml) and the mixture was stirred at 70° C. overnight. The reaction mixture was poured into ice water (15 ml), adjusted to pH 2 by adding 1N HCl, then extracted three times with chloroform (5 ml). The chloroform layer was combined, washed with saturated NaCl solution and concentrated in vacuo. The residue was purified by silica gel TLC developing with benzene-acetone (2:1) to obtain powdered 2′,4′-O-diacetyl-23-O-benzylcarbamoyl-23-demycinosyldesmycosin dimethylacetal, which was immediately dissolved in trifluoroacetic acid-2ater (9:1) and hydrolyzed at room temperature with stirring for 30 minutes. The reaction mixture was poured into ice water (20 ml), adjusted to alkaline pH (pH 9-10), and extracted three times with chloroform (10 ml). After dehydration with anhydrous magnesium sulfate, the reaction mixture was concentrated in vacuo to obtain 2′,4′-O-diacetyl-23-O-benzylcarbamoyl-23-demycinosyldesmycosin. Yield: 30%.

TLC: $Rf_c = 0.42$.

The above product was dissolved in methanol (5 ml) and stirred at 55° C. overnight. The methanol was distilled off in vacuo and the residue was dissolved in chloroform (10 ml), then washed with dil. aq. ammonia (pH 9-10). The mixture was dehydrated with anhydrous magnesium sulfate and dried in vacuo to obtain powdered 23-O-benzyl-carbamoyl-23-demycinosyldesmycosin.

Yield: 67% $Rf_b = 0.27$.

NMR (100 MHz, CDCl$_3$) $\delta_{ppm}$; 1.78 (s., 3H), 2.49 (s., 6H), 4.18 (2H), 4.25 (d., 1H), 4.36 (d., 2H), 4.93 (m., 1H), 5.09 (m., 1H), 5.81 (d., 1H), 6.72 (d., 1H), 7.27 (d., 1H), 7.29 (s., 5H), 9.69 (s., 1H).

In the above example, benzylamine (0.04 ml) was replaced by 2-aminomethylthiophene (90 mg), 2-aminothiazole (36.5 mg, added with 4-dimethylaminopyridine (30 mg)), N-methylbenzylamine (0.047 ml), N-methylaniline (0.04 ml, added with 4-dimethylaminopyridine (8 mg)) and R(+)-α-methylbenzylamine (0.047 ml) to obtain the product of the following Examples 21-25, respectively. In the examples, the reference to acetal in the results of the TLC means the intermediate for the product, i.e. 2′,4′-O-diacetyl-23-O-substituted carbamoyl-23-demycinosyldesmycosin dimethylacetal.

EXAMPLE 21

23-O-(2-thienylmethyl carbamoyl)-23-demycinosyldesmycosin: yield: 62%.

TLC: $Rf_a = 0.26$ (acetal: $Rf_c = 0.56$). NMR (100 MHz, CDCl$_3$) $\delta_{ppm}$; 1.79 (s., 3H), 2.50 (s., 6H), 4.22 (2H), 4.25 (d., 1H), 4.52 (d., 2H), 4.95 (m., 1H), 5.18 (br., 1H), 5.79 (d., 1H), 6.28 (d., 1H), 6.95 (s., 1H), 6.97 (s., 1H), 7.27 (s., 1H), 7.28 (d., 1H), 9.69 (s., 1H).

EXAMPLE 22

23-O-(2-thiazolylcarbamoyl)-23-demycinosyldesmycosin: yield: 47%

TLC: $Rf_b = 0.18$ (acetal: $Rf_c = 0.54$).

NMR (100 MHz, CDCl$_3$) $\delta_{ppm}$; 1.82 (s., 3H), 2.56 (s., 6H), 4.08 ~ 4.64 (4H), 4.98 (t.d., 1H), 5.86 (d., 1H), 6.30 (d., 1H), 6.95 (d., 1H), 7.28 (d., 1H), 7.39 (d., 1H), 9.70 (s., 1H).

EXAMPLE 23

23-O-(N-methyl-benzylcarbamoyl)-23-demycinosyldesmycosin: yield: 55%.

TLC: $Rf_b = 0.30$ (acetal $Rf_c = 0.66$).

NMR (100 MHz, CDCl$_3$) $\delta_{ppm}$; 1.79 (br.s., 3H), 2.49 (s., 6H), 2.84, 2.94 (≒ s., 3H), 4.22 (2H), 4.25 (d., 1H), 4.45 (br.s., 2H), 4.75 ~ 5.20 (aH), 5.52 ~ 5.93 (1H), 6.27 (d., 1H), 7.26 (s., 5H), 9.69 (s., 1H).

EXAMPLE 24

23-O-(N-methyl-phenylcarbamoyl)-23-demycinosyldesmycosin: yield: 73%.

TLC: $Rf_b = 0.29$ (acetal: $Rf_c = 0.77$).

NMR (100 MHz, CDCl$_3$) $\delta_{ppm}$; 1.74 (s., 3H), 2.50 (s., 6H), 3.30 (s., 3H), 4.22 (2H), 4.25 (d., 1H), 4.84 (t.d., 1H), 5.69 (d., 1H), 6.27 (d., 1H), 6.96 ~ 7.72 (m., 6H), 9.71 (s., 1H).

EXAMPLE 25

23-O-[R(+)-α-methyl-benzylcarbamoyl]-23-demycinosyldesmycosin: yield: 61%.

TLC: $Rf_b = 0.28$ (acetal $Rf_c = 0.62$).

NMR (100 MHz, CDCl$_3$) $\delta_{ppm}$; 1.48 (d., 3H), 1.78 (br. s., 3H), 2.50 (s., 6H), 4.13 (2H), 4.25 (d., 1H), 4.50 ~ 5.24 (m., 3H), 5.84 (br. d., 1H), 6.27 (d., 1H), 7.31 (s., 5H), 9.70 (s., 1H).

EXAMPLE 26

23-O-benzylthiocarbamoyl-23-demycinosyldesmycosin

2′,4′-O-diacetyl-23-demycinosyldesmycosin dimethyl acetal (100 mg) obtained in Example 19 dissolved in dichloroethane (0.5 ml) was added dropwise to a dichloroethane (1 ml) solution of 1,1′-thiocarbonylimidazole (31.4 mg, 1.2 molar excess), and then the mixture was stirred at 50° C. for 6 hours. The reaction mixture was checked by silica gel TLC developed with chloroformethanol (20:1) for the end point of the reaction, then benzylamine (0.03 ml) and 4-dimethylaminopyridine (4 mg) were added thereto, and the mixture was stirred at 70° C. overnight. The reaction mixture was poured into ice water (15 ml), adjusted to pH 2 by adding 1N HCl and extracted three times with chloroform. The chloroform layers were combined, washed with saturated sodium chloride solution and concentrated in vacuo. The residue was purified by silica gel collecting TLC developed with benzeneacetone (2:1) to obtain 2′,4′-diacetyl-23-O-benzylthiocarbamoyl-23-demycinosyldesmycosin dimethylacetal. Yield: 54%, TLC: 2′,4′-O-diacetyl-23-O-benzylthiocarbamoyl-23-demycinosyldesmycosin dimethylacetate.

Yield: TLC $Rf_g = 0.34$.

The above compound was immediately dissolved in trifluoroacetic acid-water (9:1) (1 ml) and hydrolyzed at room temperature with stirring for 30 minutes. The reaction mixture was poured into ice water (20 ml), adjusted to alkaline pH (pH 9–10) and extracted three times with chloroform (10 ml). The chloroform layers were combined and dehydrated with anhydrous magnesium sulfate and concentrated in vacuo to obtain 2',4'-O-diacetyl-23-O-benzylthio carbamoyl-23-demycinosyldesmycosin. The latter compound was dissolved in methanol (5 ml), stirred at 55° C. overnight and the methanol was distilled off in vacuo. The residue was dissolved in chloroform, washed with dil. aq. ammonia (pH 9–10), dehydrated with anhydrous magnesium sulfate and dried in vacuo to obtain 23-O-benzylthio carbamoyl-23-demycinosyldesmycosin. Yield: 53%.

TLC: $Rf_b = 0.29$.

NMR (100 MHz, CDCl$_3$) $\delta_{ppm}$; 1.79 (s., 3H), 2.50 (s., 6H), 4.25 (d., 1H), 4.31~4.64 (4H), 4.96 (m., 1H), 5.52~6.00 (1H), 6.28 (d., 1H), 7.27 (d., 1H), 7.33 (s., 6H), 9.68 (s., 1H).

EXAMPLE 27

23-[D(−)-α-methoxycarbonyl-benzyl carbamoyl]-23-demycinosyldesmycosin

In Example 20, benzylamine (0.04 ml) was replaced by D(−)-α-methoxycarbonyl benzylamine (80.3 mg) to produce 23-[D(−)-α-methoxycarbonyl benzyl carbamoyl]-23-demycinosyldesmycosin (45.6 mg).

TLC: $Rf_b = 0.29$.

NMR (100 MHz, CDCl$_3$) $\delta_{ppm}$; 1.75 (s., 3H), 2.50 (s., 6H), 3.73 (s., 3H), 4.0~4.4 (m., 2H), 4.25 (d., 1H), 4.7~5.1 (m., 1H), 5.32 (d., 1H), 5.6~5.9 (m., 2H), 6.27 (d., 1H), 7.2~7.6 (m., 6H), 9.70 (s., 1H).

EXAMPLE 28

23-O-hexamethyleneiminocarbonyl-23-demycinosyldesmycosin

The acetal compound (300 mg) in Example 19 and hexamethyleneimine (60.5 μl) were added to dichloroethane (3 ml) and the mixture was stirred at 70° C. for 2 days. The reaction mixture was poured into ice water (15 ml), adjusted to pH 2 by adding 1N-HCl and extracted three times with chloroform (5 ml). The chloroform layers were combined, washed with dil. aq. ammonia and concentrated in vacuo. The residue was purified by silica gel collecting TLC developed by hexane-benzene-ethyl acetate-methanol-acetone (90:80:60:30:25) to obtain powdered 2',4'-di-O-acetyl-23-O-hexamethyleneiminocarbonyl-23-demycinosyldesmycosin dimethylacetal (73.6 mg). The latter substance was immediately dissolved in trifluoroacetic acid-water (9:1) (1 ml) and hydrolyzed at room temperature with stirring for 30 minutes. The reaction mixture was poured into ice water (20 ml), adjusted to alkaline pH (pH 9–10) by adding aq. ammonia, and extracted three times with chloroform. The chloroform layers were dehydrated by adding anhydrous magnesium sulfate and concentrated in vacuo to obtain 2',4'-di-O-acetyl-23-O-hexamethyleneiminocarbonyl-23-demycinosyldesmycosin (57.4 mg).

TLC: $Rf_c = 0.62$.

The above compound was dissolved in methanol (5 ml) and stirred at 55° C. overnight. The methanol was distilled off, and the residue was dissolved in chloroform (10 ml), then washed with dil. aq. ammonia (pH 9–10). After dehydration with anhydrous magnesium sulfate, the mixture was dried in vacuo to obtain powdered 23-O-hexamethyleneiminocarbonyl-23-demycinosyldesmycosin (43.8 mg).

TLC: $Rf_a = 0.35$.

NMR (FX-100, CDCl$_3$) $\delta_{ppm}^{TMS}$; 1.58 (br.m., —(CH$_2$)$_4$—), 1.81 (s., 3H, C$_{12}$—CH$_3$), 2.50 (s., 6H, N(CH$_3$)$_2$), 3.40 (m., 4H, —CH$_2$—N—CH$_2$—), 4.20 (m., 3H, H-1', H-23), 4.97 (m., 1H, H-15), 5.86 (d., 1H, H-13, J=10.7 Hz), 6.29 (d., 1H,H-10, J=15.5 Hz), 7.31 (d., 1H, H-11, J=15.5 Hz), 9.70 (s., 1H, CHO).

EXAMPLE 29

23-O-heptamethyleneiminocarbonyl-23-demycinosyldesmycosin

Acetal (300 ml) and heptamethyleneimine (67.8 μl) were added to dichloroethane (3 ml) and the mixture was stirred at 70° C. overnight. The reaction mixture was poured into ice water (15 ml), adjusted to pH 2 by adding 1N HCl and extracted three times with chloroform. The chloroform layers were combined, washed with dil. aq. ammonia and concentrated in vacuo. The residue was purified by silica gel collecting TLC developed by benzene-acetone (2:1) to obtain powdered 2',4'-di-O-acetyl-23-O-heptamethyleneiminocarbonyl-23-demycinosyldesmycosin dimethyl-acetal (53.7 mg). The latter substance was immediately dissolved in trifluoroacetic acid-water (9:1) (1 ml) and hydrolyzed at room temperature with stirring for 30 minutes. The reaction mixture was poured into ice water (20 ml), adjusted to alkaline pH (pH 9–10) with aq. ammonia, and extracted three times with chloroform. The chloroform layers were combined and dehydrated by adding anhydrous magnesium sulfate and concentrated in vacuo to obtain 2',4'-di-O-acetyl-23-O-heptamethyleneiminocarbonyl-23-demycinosyldesmycosin (42.8 mg).

TLC: $Rf_c = 0.64$.

The latter substance dissolved in methanol (5 ml) was stirred at 55° C. overnight. The methanol was distilled off in vacuo and the residue dissolved in chloroform (10 ml) was washed with dil. aq. ammonia (pH 9–10). The mixture was dehydrated with anhydrous magnesium sulfate and dried in vacuo to obtain powdered 23-O-heptamethyleneiminocarbonyl-23-demycinosyldesmycosin (43.8 mg).

TLC: $Rf_a = 0.35$.

NMR (FX-100, CDCl$_3$) $\delta_{ppm}^{TMS}$; 1.53 (br. m., —(CH$_2$)$_5$—), 1.80 (s., 3H, C$_{12}$—CH$_3$), 2.50 (s., 6H, -N(CH$_3$)$_2$), 3.36 (m., 4H, —CH$_2$ —N—CH$_2$—), 4.21 (m., 3H, H-1', H-23), 4.95 (m., 1H, H-15), 5.85 (d., 1H, H-13, J=10.3 Hz), 6.29 (d., 1H, H-10, J=15.4 Hz), 7.31 (d., 1H, H-11, J=15.4 Hz), 9.70 (s., 1H, CHO).

EXAMPLE 30

2'-O-acetyl-4'-deoxy-23-demycinosyldesmycosin

Acetic anhydride (1.36 ml, 2.5 molar excess) was added dropwise to 4'-deoxy-23-demycinosyldesmycosin (3.35 g) dissolved in dichloromethane (20 ml) under ice cooling, and the mixture was stirred at room temperature for 2.5 hours. The reaction mixture was poured into dil. aq. ammonia (40 ml) and extracted twice with chloroform. The chloroform layers were combined and dehydrated with anhydrous magnesium sulfate and concentrated in vacuo to obtain 2'-O-acetyl-4'-deoxy-23-demycinosyldesmycosin (3.56 g).

NMR (FX-100, CDCl$_3$) $\delta_{ppm}^{TMS}$; 1.82 (s., 3H, C$_{12}$—CH$_3$), 2.08 (s., 3H, O COCH$_3$), 2.25 (s., 6H, -N(CH$_3$)$_2$), 3.74 (d., 2H, H-23), 4.24 (d., 1H, H-1'), 4.75 (d.d., H, H-2'), 4.96 (d. t., 1H, H-15), 5.88 (d., 1H, H-13), 6.32 (d., 1H, H-10), 7.34 (d., 1H, H-11), 9.69 (s., 1H, CHO).

Mass (CI); 6.24 (MH+), 606, 582, 218, 200.

EXAMPLE 31

2'-O-acetyl-4'-deoxy-23-O-(1-imidazolecarbonyl)-23-demycinosyldesmycosin dimethylacetal Trifluoroacetic acid (2.5 ml) was added to 2'-O-acetyl-4'-deoxy-23-demycinosyldesmycosin (5 g) dissolved in methanol (100 ml) and the mixture was stirred at room temperature for 4.5 hours. The end point of the reaction was checked by silica gel TLC showing the disappearance of a spot of the starting material and appearance of the spot at $Rf_a$ 0.43. The reaction mixture was poured into dil. aq. ammonia (250 ml) and extracted twice with chloroform (250 ml). The chloroform layers ere combined and dehydrated with anhydrous magnesium sulfate and dried in vacuo to obtain foamy 2'-O-acetyl-4'-deoxy-23-demycinosyldesmycosin dimethylacetal (4.7 g).

1,1'-carbonyldiimidazole (1.43 g, 1.2 molar excess) was added to the above acetal dissolved in dichloroethane (25 ml) and the mixture was stirred at 50° C. for 2 hours. The end point of the reaction was checked by TLC and the reaction mixture was washed with dil. HCl (pH 2-3) and dil. aq. ammonia (pH 8-10). The dichloroethane layer was dehydrated with anhydrous magnesium sulfate and concentrated in vacuo to obtain powdered 2'-O-acetyl-4'-deoxy-23-O-(1-imidazolecarbonyl)-23-demycinosyldesmycosin dimethylacetal (4.4 g).
TLC: $Rf_g$=0.2.

EXAMPLE 32

4'-deoxy-23-O-benzylcarbonyl-23-demycinosyldesmycosin

A dichloroethane (0.4 ml) solution of benzylamine (0.042 ml, 1.5 molar excess) was added to 2'-O-acetyl-4'-deoxy-23-O-(1-imidazolecarbonyl)-23-demycinosyldesmycosin dimethylacetal (200 mg) dissolved in dichloroethane (2 ml), and the mixture was stirred at 70° C. for 2 hours. The reaction mixture was washed with dil. HCl (pH 2-3) and dil. aq. ammonia (pH 8-10), dehydrated with anhydrous magnesium sulfate and concentrated in vacuo. The residue was chromatographed by silica gel collecting TLC developed by chloroform-methanol (10:1) (Merk, Art 5717, 20×20 cm, two plates), and the band was scratched showing $Rf_f$=0.41 and extracted with chloroform-methanol (2:1). The extract was dried in vacuo to obtain powdered 2'-O-acetyl-4'-deoxy-23-O-benzylcarbonyl-23-demycinosyldesmycosin dimethylacetal (50.8 mg).
TLC: $Rf_f$=0.41.

Cold trifluoroacetic acid-water (9:1 v/v) (1 ml) was added to the above product and the mixture was stirred under ice cooling for 30 minutes. The end point of the reaction was checked by TLC, and the reaction mixture was poured into ice water, then adjusted to pH 8-10. The mixture was extracted twice with chloroform and the extract was dehydrated with anhydrous magnesium sulfate, then concentrated in vacuo. The residue, dissolved in methanol (5 ml), was stirred at 55° C. overnight, and concentrated in vacuo. The residue was dissolved in chloroform and washed with dil. aq. ammonia. The chloroform layer was dehydrated with anhydrous magnesium sulfate and dried in vacuo to obtain was a powder 4'-deoxy-23-O-benzylcarbamoyl-23-demycinosyldesmycosin
TLC; Rfb=0.57.

NMR (FX-100, CDCl₃); $\delta_{ppm}$; 1.77 (s., 3H, $C_{12}$—$CH_3$), 2.26 (s., 6H, -N $(CH_3)_2$), 4.12~4.24 (3H, H-23, H-1'), 4.36 (d., 2H, J=5.9 Hz, Ph—$CH_2$—NH—), 4.80~5.30 (m., 2H, H-15, NH), 5.83 (d., 1H, J=9.6 Hz, H-13), 6.30 (d., 1H, J=15.2 Hz, H-10), 7.18~7.60 (6H, phenyl proton, H-11), 9.72 (s., 1H, CHO).

EXAMPLE 33

4'-deoxy-23-O-[L-(−)-α-phenylethyl]carbamoyl-23-demycinosyldesmycosin

In Example 32, benzylamine was replaced by L-(−)-α-phenylethylamine (1.5 molar excess) to produce a powder of 4'-deoxy-23-O-[L-(−)-α-phenylethyl]carbamoyl-23-demycinosyldesmycosin (34.1 mg).

NMR (FX-100, CDCl₃) $\delta_{ppm}$; 1.48 (d., 3H, J=6.6 Hz,

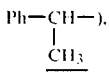

1.74 (s., 3H, $C_{12}$—$CH_3$), 2.26 (s., 6H, -N $(CH_3)_2$), 4.04~4.40 (3H, H-23, H-1'), 4.50~5.20 (m., 3H, H-15, NH

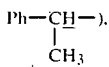

5.80 (d., 1H, J=11 Hz., H-13), 6.29 (d., 1H, J=15.7 Hz, H-10), 7.18 ~7.44 (6H, H-11), 9.72 (s., 1H, CHO).

EXAMPLE 34

4'-deoxy-23-O-(p-chlorophenylcarbamoyl)-23-demycinosyldesmycosin p-chloroaniline (1.5 molar excess) and a catalytic amount of a dichloroethane solution (0.4 ml) of dimethylaminopyridine were added to 2'-O-acetyl-4'-deoxy-23-O-(1-imidazole carbonyl)-23-demycinosyldesmycosin dimethylacetal (200 mg) dissolved in dichloroethane (2 ml) and the mixture was stirred at 70° C. for 4 days. The reaction mixture was washed with dil. HCl (pH 2-3) and dil. aq. ammonia (pH 8-10), and the dichloroethane layer was dehydrated with anhydrous magnesium sulfate, then concentrated in vacuo. The residue was chromatographed with collecting TLC developed by chloroform-methanol (10:1) (Merck, Art 5717, 20×20 cm, two plates) and the band was scratched showing $Rf_f$ 0.4, and extracted with chloroform-methanol (2:1). The extract was dried in vacuo to obtain a powder of 2'-O-acetyl-4'-deoxy-23-O-(p-chlorophenylcarbamoyl)-23-demycinosyldesmycosin dimethylacetal (42.3 mg).

The acetal of the latter substance was hydrolyzed and the '-O-acetyl group was removed in the same way as in Example 32, to obtain a powder of 4'-deoxy-23-O-(p-chlorophenyl carbamoyl)-23-demycinosyldesmycosin (27.8 mg).
TLC; Rfb=0.56

NMR (FX-100, CDCl₃) $\delta_{ppm}$; 1.80 (s., 3H, $C_{12}$-$CH_3$), 2.26 (s., 6H, -$N(CH_3)_2$), 4.15~4.36 (3H, H-23, H-1'), 4.97 (1H, H-15), 5.88 (d., 1H, J=11 Hz, H-13), 6.32 (d., 1H, J=16.0 Hz, H-10), 6.85 (s., 1H, -NH), 7.16~7.62 (p-chlorophenyl proton, H-11), 9.71 (s., 1H, CHO).

EXAMPLE 35

23-O-(β-phenylethyl carbamoyl)-23-demycinosyldesmycosin

In Example 20, benzylamine (0.04 ml) was replaced by β-phenylethylamine (0.046 ml) to obtain 23-O-(β-phenylethyl carbamoyl)-23-demycinosyldesmycosin (53.8 mg).

NMR (100 MHz, CDCl₃) $\delta_{ppm}$: 1.80(s., 3H), 2.50(s., 6H), 4.25 (d., 1H), 4.79 (t., 1H), 4.92 (d.t., 1H), 5.80 (d., 1H), 6.28 (d., 1H), 7.27 (s. 5H), 7.30 (d., 1HO,9.69 (s., 1H).

Example 36

23-O-[R(+)-α-methyl-benzylthiocarbamoyl]-23-demycinosyldesmycosin

In Example 26, benzylamine (0.03 ml) was replaced by R(+)-α-methylbenzylamine (0.035 ml) to produce the above-mentioned product (36.2 mg).

NMR (100 MHz, CDCl₃) $\delta_{ppm}$: 1.47, 1.58 (each d., 3H), 1.67, 1.81 (each s., 3H), 2.50 (s, 6H), 4.27(d., 1H), 6.21, 6.29 (each d., 1H), 734 (s., 5H), 9.70, 9.75 (each s., 1H).

EXAMPLE 37

23-O-[S(−)-α-methyl benzyl thiocarbamoyl]-23-demycinosyldesmycosin

In Example 26, benzylamine (0.03 ml) was replaced by S(−)-α-methylbenzylamine (0.035 ml) to produce the above-mentioned product (45.0 mg).

NMR (100 MHz, CDCl₃) $\delta_{ppm}$: 1.49, 1.58 (each d.,

1.77 (s., C₂—CH₃), 4.25 (d., H-1'), 5.78 (d. t., H-13), 6.29 (d., H-10), 7.29, 7.32 (each s., phenyl), 9.72 (s., CHO).

EXAMPLE 38

23-O-(N-methyl benzylthiocarbamoyl)-23-demycinosyldesmycosin

In Example 26, benzylamine (0.03 ml) was replaced by N-methyl-benzylamine (0.035 ml) to produce the above-mentioned product (12.0 mg).

NMR (100 MHz, CDCl₃) $\delta_{ppm}$: 1.72, 1.82 (each s., 3H), 2.62 (s., 6H), 2.91 (s., 3H), 4.29 (d., 1H), 4.50 (s., 2H), 5.59, 5.87 (each d., 1H), 6.21, 6.29 (each d., 1H), 7.31 (s., 5H), 9.70 (s., 1H).

EXAMPLE 39

4'-deoxy-23-O-hexamethyleneiminocarbonyl-23-demycinosyldesmycosin

Hexamethyleneimine (75 μl, 1.5 molar excess) was added to acetal (160 mg) obtained in Example 31 dissolved in dichloroethane (6 ml) and the mixture was stirred at 70° C. for 2 days. The reaction mixture was adjusted to pH 2 by adding 1N HCl and extracted three times with chloroform (5 ml). The chloroform layers were combined and washed with water, dehydrated with anhydrous magnesium sulfate and concentrated in vacuo to obtain the crude product (165 mg), which was purified by silica gel collecting TLC (Merck, Art 5717, 20×20 cm) developed by chloroform-methanol (15:1). The band showing Rf$_a$ 0.3 was scratched and extracted with chloroform-methanol (3:1). The extract was dried in vacuo to obtain 2'-O-4'-deoxy-23-O-hexamethyleneiminocarbonyl-23-demycinosyldesmycosin dimethylacetal (74 mg), which was dissolved in methanol (5 ml) and the mixture was stirred at 55° C. for 15 hours. The methanol was distilled off in vacuo, and trifluoroacetic acid-water (9:1) (1 ml) was added to the residue under ice cooling, then the mixture was stirred at room temperature for 30 minutes. The reaction mixture was poured into ice water (20 ml), adjusted to pH 9.5 by adding aq. ammonia and extracted three times with chloroform (10 ml). The chloroform layers were combined and dehydrated with anhydrous magnesium sulfate and concentrated in vacuo to obtain white foamy 4'-deoxy-23-O-hexamethyleneiminocarbonyl-23-demycinosyldesmycosin (50 mg).

NMR (FX-100, CDCl₃) $\delta_{ppm}^{TMS}$: 1.4–1.8 (m., 8, —(CH₂)₄—), 1.79 (s., 3H, C₁₂—CH₂), 2.26 (s., 6H, —N(CH₃)₂), 3.2–3.6 (m., 4H, —CH₂—N—CH₂), 4.17–4.24 (m., 3H, H-1', H-23), 4.96 (d., t., 1H, H-15), 5.86 (d., 1H, H-13), 6.31 (d., 1H, H-10), 9.72 (s., 1H, CHO).

Mass (CI): 707(MH⁺), 176, 158.

What is claimed is:

1. A compound of the formula

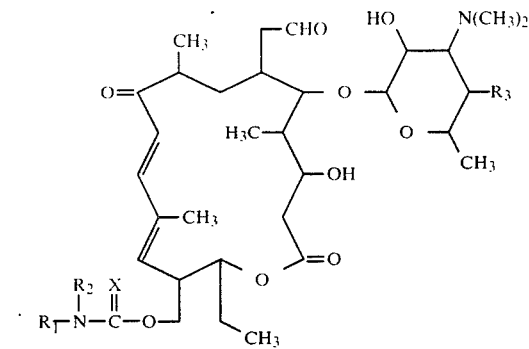

wherein R₁ is lower alkyl, lower alkoxycarbonyl-lower alkyl, phenyl, phenyl substituted by one or more lower alkyl or halogen, phenyl-lower alkyl optionally substituted in its side chain by lower alkyl or lower alkoxycarbonyl, thienylmethyl or thiazolyl, R₂ is hydrogen or lower alkyl, or

constitutes a 3–7-membered nitrogen-containing heterocyclic ring in which R₁ and R₂ are connected, R₃ is hydrogen or hydroxyl, and X is oxygen or sulfur, or a non-toxic salt thereof.

2. A compound according to claim 1 wherein the said compound is a compound selected from the group consisting of the following:

23-O-(2,5-dichlorophenylcarbamoyl)-23-demycinosyldesmycosin,

23-O-(p-chlorophenyl carbamoyl)-23-demycinosyldesmycosin,

23-O-(p-fluorophenyl carbamoyl)-23-demycinosyldesmycosin,

23-O-(p-tolyl carbamoyl)-23-demycinosyldesmycosin,

23-O-[S(−)-α-methylbenzyl carbamoyl]-23-demycinosyldesmycosin,

23-O-ethoxycarbonylmethyl carbamoyl-23-demycinosyldesmycosin,
23-O-propyl carbamoyl-23-demycinosyldesmycosin,
23-O-butyl carbamoyl-23-demycinosyldesmycosin,
23-O-benzylthio carbamoyl-23-demycinosyldesmycosin,
23-O-benzyl carbamoyl-23-demycinosyldesmycosin,
23-O-(β-phenylethyl carbamoyl)-23-demycinosyldesmycosin,
23-O-[R(+)-α-methyl-benzylthio carbamoyl]-23-demycinosyldesmycosin,
23-O-[S(−)-α-methyl-benzylthio carbamoyl]-23-demycinosyldesmycosin,
23-O-(N-methyl-benzylthio carbamoyl)-23-demycinosyldesmycosin,
23-O-(2-thienylmethyl carbamoyl)-23-demycinosyldesmycosin,
23-O-(thiazolyl carbamoyl)-23-demycinosyldesmycosin,
23-O-(N-methyl-benzyl carbamoyl)-23-demycinosyldesmycosin,
23-O-(N-methyl-phenyl carbamoyl)-23-demycinosyldesmycosin,
23-O-[R(+)-α-methyl-benzyl carbamoyl]-23-demycinosyldesmycosin,
23-O-[D(−)-α-methoxycarbonyl-benzyl carbamoyl]-23-demycinosyldesmycosin,
23-O-hexamethyleneiminocarbonyl-23-demycinosyldesmycosin,
23-O-heptamethyleneiminocarbonyl-23-demycinosyldesmycosin,
4′-deoxy-23-O-hexamethyleneiminocarbonyl-23-demycinosyldesmycosin,
4′-deoxy-23-O-benzyl carbamoyl-23-demycinosyldesmycosin,
4′-deoxy-23-O-[L(−)-α-phenylethyl]carbamoyl-23-demycinosyldesmycosin, and
4′-deoxy-23-O-(p-chlorophenylcarbamoyl)-23-demycinosyldesmycosin.

* * * * *